(12) United States Patent
Attolino et al.

(10) Patent No.: US 8,969,561 B2
(45) Date of Patent: Mar. 3, 2015

(54) APIXABAN PREPARATION PROCESS

(71) Applicant: Dipharma Francis S.r.l., Baranzate (MI) (IT)

(72) Inventors: Emanuele Attolino, Baranzate (IT); Alessandro Lombardo, Baranzate (IT); Simone Tambini, Baranzate (IT)

(73) Assignee: Dipharma Francis S.r.l., Baranzate (MI) (IT)

( * ) Notice: Subject to any disclaimer, the term of this patent is extended or adjusted under 35 U.S.C. 154(b) by 0 days.

(21) Appl. No.: 14/511,374

(22) Filed: Oct. 10, 2014

(65) Prior Publication Data

US 2015/0025242 A1 Jan. 22, 2015

Related U.S. Application Data

(62) Division of application No. 14/110,966, filed as application No. PCT/EP2012/060800 on Jun. 7, 2012, now Pat. No. 8,884,016.

(30) Foreign Application Priority Data

Jun. 10, 2011 (IT) .............................. MI2011A1047
Jun. 22, 2011 (IT) .............................. MI2011A1135

(51) Int. Cl.
*C07D 471/04* (2006.01)
*C07F 7/18* (2006.01)
*C07D 211/86* (2006.01)

(52) U.S. Cl.
CPC ............ *C07D 471/04* (2013.01); *C07F 7/1896* (2013.01); *C07D 211/86* (2013.01)
USPC .............................. 546/14; 546/120; 546/294

(58) Field of Classification Search
USPC ............................................ 546/14, 120, 294
See application file for complete search history.

(56) References Cited

U.S. PATENT DOCUMENTS

| 6,967,208 | B2 | 11/2005 | Pinto |
| 7,153,960 | B2 | 12/2006 | Zhou |
| 7,312,214 | B2 * | 12/2007 | Qiao et al. .................. 514/230.5 |
| 7,396,932 | B2 | 7/2008 | Shapiro |
| 2005/0245566 | A1 | 11/2005 | Zhou et al. |
| 2006/0069258 | A1 | 3/2006 | Shapiro et al. |
| 2006/0160841 | A1 | 7/2006 | Wei et al. |

FOREIGN PATENT DOCUMENTS

WO        03/026652 A1    4/2003

OTHER PUBLICATIONS

Pinto et al., "Discovery of 1-[4-(Methoxyphenyl)-7-oxo-6-(4-(2-oxopipe ridin-1-yl)phenyl)-4,5,6,7-tetrahydro-1H-pyrazolo [3,4-c]pyridine-3-carboxamide )Apixaban . . . ", Journal of Medicinal Chemistry, vol. 50, Jan. 1, 2007, pp. 5339-5356.

* cited by examiner

*Primary Examiner* — Niloofar Rahmani
(74) *Attorney, Agent, or Firm* — Rothwell, Figg, Ernst & Manbeck, P.C.

(57) ABSTRACT

Process for the preparation of apixaban and intermediates useful for the preparation thereof.

13 Claims, 2 Drawing Sheets

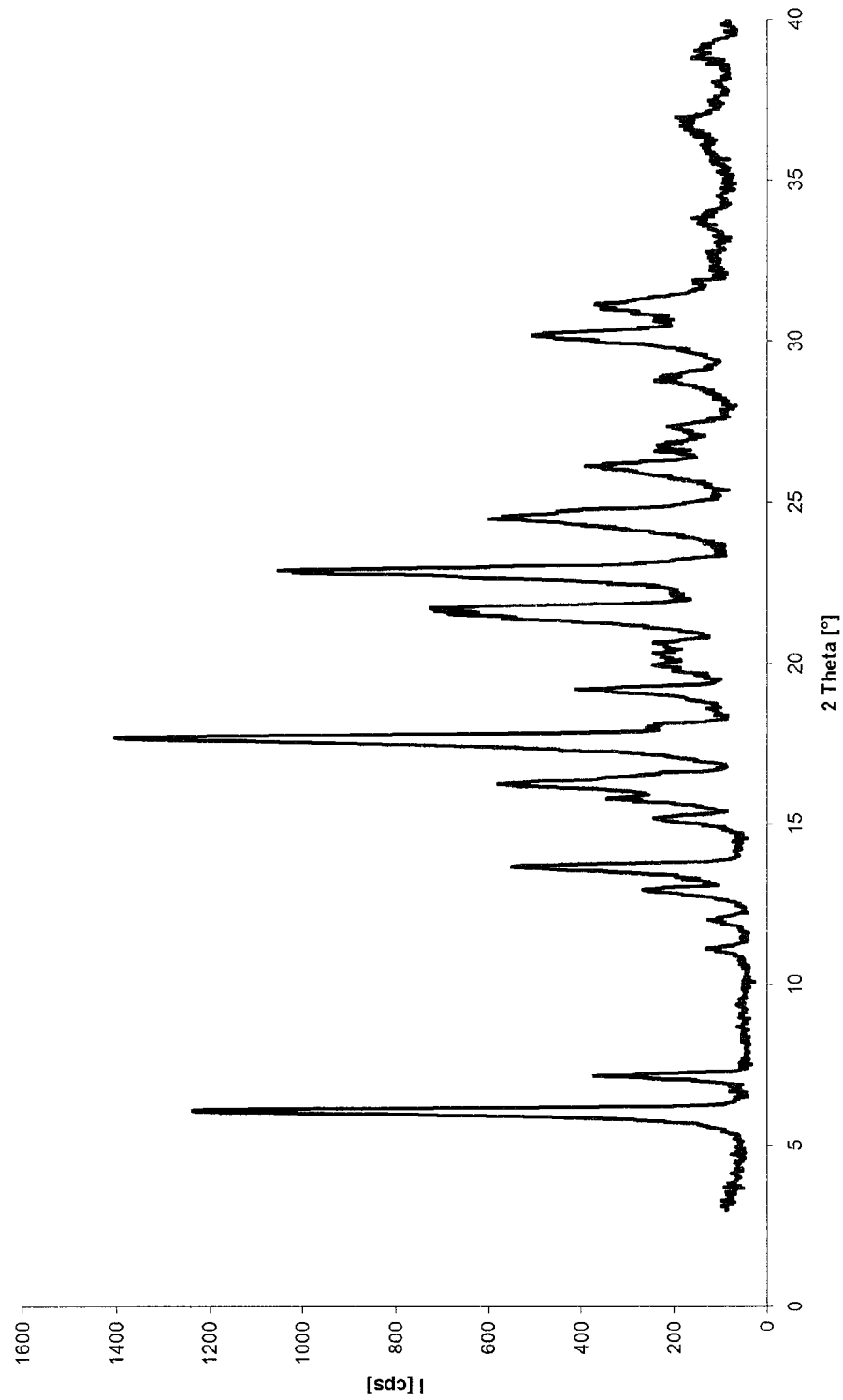
Figure 1. XRPD of Apixaban form α

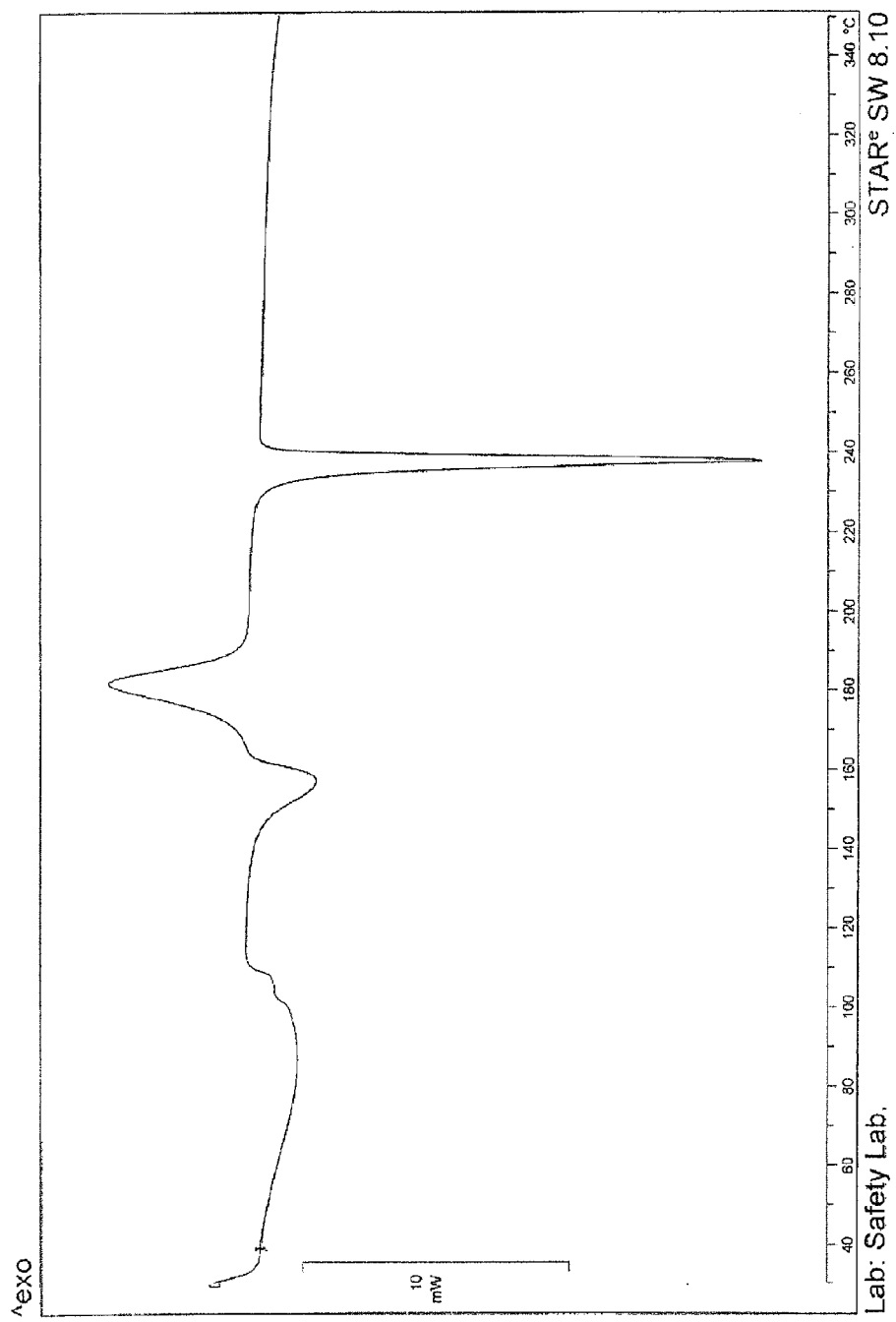
Figure 2. DSC trace of apixaban form α

APIXABAN PREPARATION PROCESS

This application is a divisional of U.S. Ser. No. 14/110,966 filed Oct. 10, 2013, which is a 35 U.S.C. 371 National Phase Entry Application from PCT/EP2012/060800, filed Jun. 7, 2012, which claims the benefit of Italian Patent Application Nos. MI2011 A001047 filed on Jun. 10, 2011 and MI2011 A001135 filed on Jun. 22, 2011, the disclosures of which are incorporated herein in their entirety by reference.

FIELD OF INVENTION

The present invention relates to a novel process for the preparation of apixaban and synthetic intermediates useful for the preparation thereof.

PRIOR ART

I-(4-Methoxyphenyl)-7-oxo-6-[4-(2-oxopiperidin-I-yl)phenyl]-4,5,6,7-tetrahydro-IH-pyrazolo[3,4-c]pyridine-3-carboxyamide of formula (I), also known come apixaban, is a powerful inhibitor of coagulation factor Xa disclosed in U.S. Pat. No. 6,967,208. Said compound is used in the prevention and treatment of thromboembolic disorders.

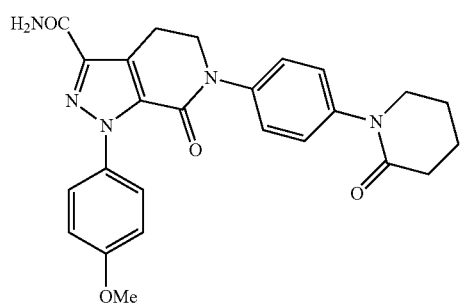

U.S. Pat. No. 7,153,960 discloses a process for the preparation of apixaban wherein the key step is the formation of intermediate (A) by 1,3 dipolar cycloaddition reaction between the compounds of formula (B) and (C) and its subsequent conversion to the compound of formula (D) by treatment with an acid. The compound of formula (D), after simple manipulations of functional groups, is converted to apixaban

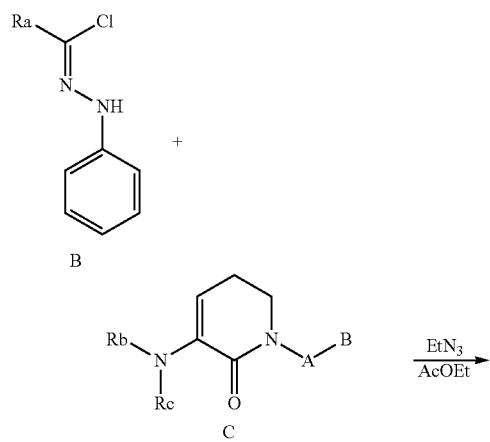

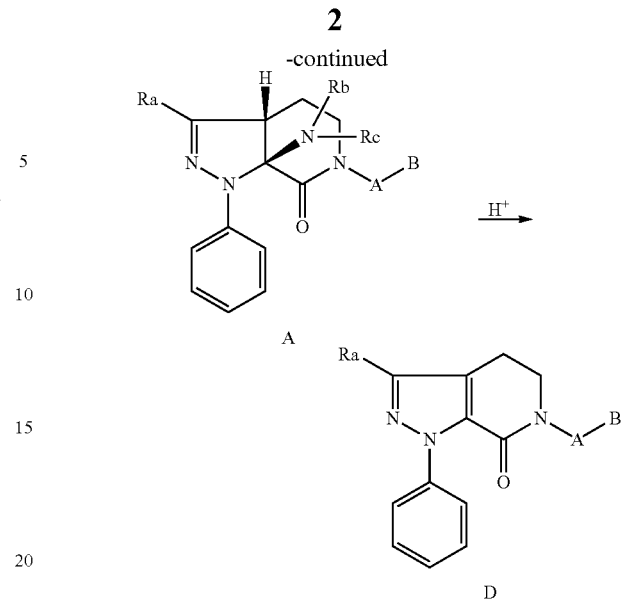

Said patent discloses the preparation of the compounds of formula (B) and (C). While the synthesis of the hydrazone of formula (B) has been known for some time, the preparation of the key intermediate of formula (C) is complex and uses reagents which are expensive and potentially hazardous, such as phosphorus pentachloride ($PCl_5$), and drastic reaction conditions.

U.S. Pat. No. 7,153,960, for example, discloses as preferred the preparation of an enamine intermediate of formula (C) wherein the amine residue $NR_bR_c$ is a morpholine. The conditions used for the success of the reaction actually involve the use of morpholine as solvent at high temperatures, such as reflux temperature (about 130-135° C.).

The complexity of the known processes for the preparation of the intermediate of formula C, the expense and danger of the reagents and the drastic reaction conditions used make said processes difficult to apply and scale up industrially, especially for the purpose of preparing the intermediates of formula A and D and apixaban.

There is consequently a need for an alternative method for the preparation of apixaban and its intermediates which does not involves the problems described above. Said method should in particular be more industrially scalable, allow the desired compounds to be obtained with high yields, and use cheaper reagents which are simpler to handle, also using mild reaction conditions.

SUMMARY OF THE INVENTION

It has surprisingly been found that a compound of formula (II) or a salt thereof

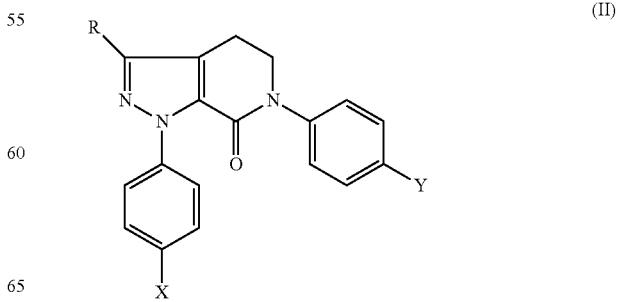

can be advantageously prepared by cycloaddition between a compound of formula (III)

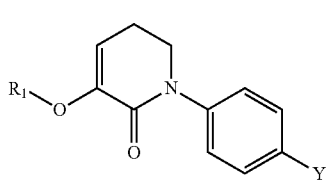

(III)

and a compound of formula (IV)

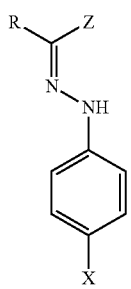

(IV)

wherein R, $R_1$, X, Y and Z are as defined below.

A compound of formula (III) is novel, and its use in the synthesis of a compound of formula (II) is surprisingly advantageous, as it enables said compound of formula (II) to be obtained easily, with high yields and total regioselectivity.

The cycloaddition reaction between a compound of formula (III) and a compound of formula (IV), like the synthesis of the novel intermediate of formula (III) according to the invention, involves the use of safe, cheap reagents and low reaction temperatures. The process according to the invention is particularly advantageous for that reason.

It has also been found that apixaban of formula (I) can exist in a hydrated crystalline form, here called Form α, containing about 1.5 moles of water per mole of apixaban, so that it can be described as substantially sesquihydrated.

Said crystalline form is particularly useful as an intermediate in the preparation of the commercially available crystalline forms of apixaban. In fact, it has surprisingly been found that novel crystalline form α is easily filterable, very stable on drying and easily handled. Said particular properties make said crystalline form particularly suitable for use in industrial processes for the preparation of the commercially available crystalline forms of apixaban. They can thus be obtained easily, with high yields and chemical purity.

BRIEF DESCRIPTION OF ANALYSIS METHODS AND FIGURES

Apixaban Form α was characterised by X-ray powder diffraction (XRPD) and differential scanning calorimetry (DSC). The water content of the compounds was determined by titration with the Karl Fischer technique. The X-ray diffraction spectra (XRPD) were collected with the APD-2000 automatic powder and liquid diffractometer manufactured by Ital-Structures, under the following operating conditions: CuKα radiation (λ=1.5418 Å), scanning with a 2θ angle range of 3-40°, with a step size of 0.03° for 1 sec. The DSC thermograms were acquired with a Mettler-Toledo DSC 822e differential scanning calorimeter, under the following operating conditions: open aluminium capsule, range 30-300° C. at the rate of 10° C./min, with nitrogen as purge gas (80 ml/min).

FIG. 1: XRPD spectrum of apixaban Form α.

FIG. 2: DSC trace of apixaban Form α.

DETAILED DESCRIPTION OF THE INVENTION

Object of the present invention is a process for the preparation of a compound of formula (II), as a single stereoisomer or a mixture thereof, or a salt thereof (II)

wherein each of X and Y, which are the same or different, is an optionally substituted $C_1$-$C_{12}$ alkyl group; an optionally substituted $C_3$-$C_{12}$ cycloalkyl group; an optionally substituted aryl group; an optionally substituted $C_1$-$C_{12}$ alkoxy group; a halogen; hydroxy; cyano; nitro; an amine group —NR'R" or an amide group —NR'COR", wherein each of R' and R", which are the same or different, is hydrogen; an optionally substituted $C_1$-$C_{12}$ alkyl group; an optionally substituted $C_3$-$C_{12}$ cycloalkyl group; an optionally substituted aryl group; or R' and R", taken together, complete a heterocyclic $C_2$-$C_7$ ring;

R is an optionally substituted $C_1$-$C_{12}$ alkyl group; an optionally substituted $C_3$-$C_{12}$ cycloalkyl group; an optionally substituted aryl group; cyano; a COOR' group, wherein R' is as defined above; a —CONR'R" group, wherein each of R' and R", which are the same or different, is as defined above;

comprising:

the cycloaddition reaction between a compound of formula (III)

(III)

wherein Y is as defined above; and $R_1$ is an optionally substituted $C_3$-$C_{12}$ cycloalkyl group; an optionally substituted aryl-$C_1$-$C_{12}$ alkyl group; a silyl group of formula $(R_2)_3Si$—, wherein each $R_2$, being the same or different, is selected from the group comprising optionally substituted $C_1$-$C_{12}$ alkyl, optionally substituted $C_3$-$C_{12}$ cycloalkyl, optionally substituted $C_1$-$C_{12}$ alkoxy and optionally substituted aryl; or a sulphonyl group $R_3SO_2$—, wherein $R_3$ is an optionally substituted $C_1$-$C_{12}$ alkyl group, an optionally substituted $C_3$-$C_{12}$ cycloalkyl group, an optionally substituted aryl group, an optionally substituted aryl-$C_1$-$C_{12}$ alkyl group; or an $R_3CO$-acyl group wherein $R_3$ is as defined above;

and a compound of formula (IV)

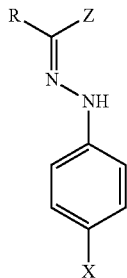

(IV)

wherein Z is halogen or a sulphonyl group of formula $R_3SO_2$—O—, wherein $R_3$ is as defined above; and R and X are as defined above; and, if appropriate, the conversion of a compound of formula (II) to another compound of formula (II), and/or the resolution of a mixture of its stereoisomers into a single stereoisomer, and/or the conversion of a compound of formula (II) to a salt thereof, and/or the conversion of a salt of a compound of formula (II) to a free compound of formula (II).

A salt of a compound of formula (II) is typically a pharmaceutically acceptable salt, as known, for example, from U.S. Pat. No. 6,967,208.

A compound of formula (II) or a pharmaceutically acceptable salt thereof may be in crystalline or amorphous, solvated or hydrated form.

A $C_1$-$C_{12}$ alkyl group, straight or branched, is typically a $C_1$-$C_6$ alkyl group such as methyl, ethyl, n-propyl, isopropyl, n-butyl, isobutyl or tert-butyl; in particular methyl or tert-butyl.

A $C_1$-$C_1$, alkoxy group, straight or branched, is, for example, methoxy, ethoxy, n-propoxy, isopropoxy, n-butoxy, isobutoxy or tert-butoxy; in particular methoxy or tert-butoxy.

A $C_1$-$C_{12}$ alkyl group can typically be a $C_1$-$C_4$ alkyl group substituted by one, two or three substituents, preferably one or two, independently selected from halogen, preferably fluorine or chlorine; hydroxy; acetoxy and $C_1$-$C_4$ alkoxy.

A $C_3$-$C_{12}$ cycloalkyl group can be, for example, cyclopropyl, cyclopentyl or cyclohexyl, preferably cyclohexyl.

An aryl group can be, for example, a $C_6$-$C_{12}$ aryl group, preferably phenyl or naphthyl, in particular phenyl.

An aryl-$C_6$-$C_{12}$ alkyl group is, for example, benzyl or phenylethyl, preferably benzyl, wherein the alkyl is not substituted or is substituted by one, two or three, preferably one or two, substituents selected independently from halogen, hydroxy, acetoxy and $C_1$-$C_4$ alkoxy.

A $C_2$-$C_7$ heterocyclic ring is preferably a saturated or unsaturated $C_5$-$C_6$ heterocyclic ring.

A halogen is preferably chlorine, bromine or iodine.

The compounds of the invention, in particular those wherein substituents X and/or Y are an alkyl group, may exist as a single stereoisomer or a mixture thereof.

The cycloaddition reaction can be carried out in a solvent, and optionally in the presence of a base.

A solvent can be, for example, a polar aprotic solvent, typically an amide, such as dimethylformamide, dimethylacetamide or N-methylpyrrolidone, preferably dimethylacetamide, acetonitrile or dimethyl sulphoxide; or a solvent selected from an ether, such as tetrahydrofuran or dioxane; a chlorinated solvent, such as dichloromethane, dichloroethane, chloroform or chlorobenzene; an ester, such as ethyl or methyl acetate; an apolar aprotic solvent, typically toluene; a polar protic solvent, typically an alkanol, and preferably a $C_1$-$C_5$ alkanol; water and a mixture of two or more, preferably two or three, of said solvents.

In accordance with a preferred aspect of the invention, the cycloaddition reaction is effected in the presence of ethyl acetate.

A base can be organic or inorganic, strong or weak base.

An organic base can be, for example, a cyclic or acyclic tertiary amine, such as trimethylamine or triethylamine, preferably triethylamine, or an alkali metal $C_1$-$C_6$ alkoxide, for example sodium or potassium, preferably potassium tert-butoxide.

An inorganic base can be selected, for example, from a carbonate, a hydroxide or a hydride of an alkali metal, for example of sodium or potassium, or an alkaline earth metal, such as calcium. Said base is preferably a sodium or potassium carbonate, hydroxide or hydride.

The cycloaddition reaction is preferably carried out in the presence of triethylamine, and more preferably in the presence of ethyl acetate and triethylamine.

The reaction can be effected at a temperature of between about 0° C. and the solvent reflux temperature, preferably between about 40° C. and about 85° C.

If, in a compound of formula (III), $R_1$ is an optionally substituted $C_3$-$C_{12}$ cycloalkyl group, optionally substituted aryl-$C_1$-$C_{12}$ alkyl group or silyl group of formula $(R_2)_3Si$—, as defined above, at the end of the cycloaddition reaction said process also includes treatment of the reaction mixture with an aqueous acid. The aqueous acid can be organic or inorganic, weak or strong, preferably hydrochloric acid, typically 37% hydrochloric acid. In a compound of formula (III), $R_1$ is preferably an $(R_2)_3Si$— group, wherein $R_1$ is an optionally substituted $C_1$-$C_4$ alkyl group.

A compound of formula (II) wherein R is $CONH_2$, X is —$OCH_3$ and Y is a —NR'COR'' amide group wherein R' and R'', taken together, complete a heterocyclic $C_6$ ring, is apixaban of formula (I). In accordance with a particularly preferred aspect of the invention, a compound of formula (II) is apixaban of formula (I).

A compound of formula (II), or a salt thereof, can be converted to another compound of formula (II), such as apixaban of formula (I), according to known methods, as reported in U.S. Pat. No. 6,967,208.

The resolution of a mixture of the stereoisomers of a compound of formula (II) to a single stereoisomer, the conversion of a compound of formula (II) to a salt thereof, and the conversion of a salt of a compound of formula (H) to an unsalified compound of formula (II) can be performed according to known methods.

A compound of formula (I), namely apixaban, obtained by the process according to the present invention, can be in a crystalline form known from U.S. Pat. No. 7,396,932, as obtainable by the isolation techniques reported therein. According to a further aspect of the invention, a novel hydrated crystalline form of apixaban is provided, and in particular a sesquihydrate, here called Form α.

Said crystalline form α is particularly pure and thus very useful to obtain apixaban in any of the commercially available forms, such as those known from U.S. Pat. No. 7,396,932, such as H2-2 and N-2, with high yields and chemical purity.

A further subject of the present invention is therefore a process for the preparation of apixaban of formula (I) in crystalline forms H2-2 and N-2, which comprises the use of said novel crystalline form α as starting material.

Said novel crystalline form α presents an XRPD as substantially reported in FIG. 1, where the most intense peaks are observed at 6.0, 7.1, 11.0, 11.9, 12.9, 13.6, 15.1, 16.1, 17.6, 19.1, 20.3, 21.6, 22.7, 24.5, 26.0, 26.7, 27.2, 28.8 and 30.1° in 2θ.

It is also characterised by a DSC thermogram as substantially reported in FIG. 2, where the main thermal events are observed at about 60-110° C. (endothermy), 145-155° C. (endothermy), 175-185° C. (exothermy) and 234° C. (melting endothermy).

Said Form α also has a water content of between about 3 and 7% w/w, preferably between about 4.5 and 6.5% w/w, and more preferably between about 5 and 6% w/w, so that it can be substantially described as a sesquihydrate.

According to one aspect of the invention, the crystalline form α of apixaban can be prepared by a process comprising:
forming a dispersion of apixaban in a solvent mixture;
cooling of the dispersion; and
recovering of the solid.

A dispersion of apixaban can be prepared using as starting material, for example, crude apixaban as obtainable by the novel synthesis process according to the invention. Alternatively, any known solid form thereof can be used, in particular the dihydrate crystalline form H2-2, known from U.S. Pat. No. 7,396,932.

The concentration of apixaban in the starting dispersion can be between about 0.1 and 50% w/w, preferably between about 2 and 20% w/w.

The solvent mixture comprises water and optionally a solvent selected, for example, from the group comprising an ether, preferably tetrahydrofuran (THF); a ketone, such as a $C_3$-$C_7$ ketone, preferably acetone, methyl isobutyl ketone, methyl ethyl ketone and diethyl ketone, in particular acetone; an ester, preferably ethyl acetate; an aliphatic or aromatic hydrocarbon, preferably hexane, heptane and toluene; a polar protic solvent, such as an alcohol, for example a $C_1$-$C_6$ alkanol optionally substituted by halogen, preferably trifluoroethanol, methanol, ethanol and isopropanol; a high-boiling polar solvent, such as an amide, in particular dimethylacetamide, or a sulphoxide, in particular dimethyl sulphoxide; or a mixture of two or more, preferably two or three, of the solvents specified above.

If a crystalline form of apixaban containing at least 1.5 moles of water, such as the dihydrate crystalline form H2-2, is used as starting material, it is unnecessary for the solvent mixture used in the process to contain water. Conversely, if the starting material is a crystalline form with a lower water content, such as the anhydrous form N-1, the solvent mixture must necessarily contain water.

The dispersion of apixaban in the solvent mixture can be formed by heating the mixture, for example to the reflux temperature of the solvent mixture.

According to a further aspect of the invention, the dispersion of apixaban in the solvent mixture can be the same, already formed, as obtainable by the synthesis method of the product.

The dispersion can be cooled by reducing its temperature to a value typically between −10° C. and 30° C.; for example by reducing the temperature at a rate of between about 0.05° C./min and 30° C./min so as to increase the formation of crystalline form α.

The formation of crystalline form α can be obtained by optionally seeding, before or during cooling, with crystals of said crystalline form α, previously obtained according to the method here described, thus promoting crystallisation.

Apixaban Form α can be recovered by one of the known techniques, such as filtration or centrifugation, preferably filtration.

The recovered product can be dried according to known methods, such as exposure to air or heating, for example between 25 and 50° C., preferably under vacuum.

Said Form α, as thus obtainable, has a water content of between about 3 and 7% w/w, preferably between about 4.5 and 6.5% w/w, and more preferably between about 5 and 6% w/w, so that it can be substantially described as a sesquihydrate.

The size of the crystals of apixaban crystalline form α, as obtainable by the process described above, is characterised by a $D_{50}$ value of between about 25 and 250 μm. If desired, said value can be reduced by micronisation or fine grinding.

The purity of apixaban form α, as obtainable according to the present invention, is equal to or greater than 99.5%, in particular equal to or greater than 99.9%.

Object of the present invention is also a pharmaceutical composition containing as active ingredient at least the crystalline form of apixaban defined here as Form α, and a pharmaceutically acceptable excipient and/or carrier. Said pharmaceutical composition can be prepared in a pharmaceutical form according to the methods known in pharmaceutical technology. The dosage of active ingredient present in said composition can be that commonly used in clinical practice for apixaban, although the choice of said dosage is left to the physician.

A compound of formula (III) can be prepared by a process comprising the reaction between the ketolactam of formula (V),

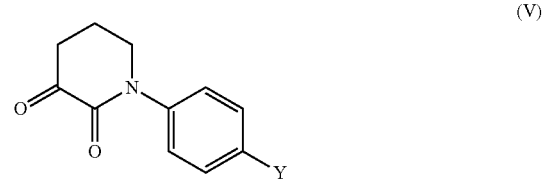

(V)

wherein Y is as defined previously, and a compound of formula (VI)

$R_1W$ (VI)

wherein $R_1$ is as defined above and W is a leaving group, for example a halogen as defined above or a sulphonate group of formula $R_3SO_3$—, wherein $R_3$ is as defined previously.

A compound of formula (VI) according to the invention is preferably a compound of formula $(CH_3)_3$—SiCl or TsCl (tosyl chloride).

The reaction between a compound of formula (V) and a compound of formula (VI) can be carried out in the presence of a base and, if desired, of a solvent.

A solvent can be, for example, a polar aprotic solvent, typically an amide, such as dimethylformamide, dimethylacetamide or N-methylpyrrolidone, preferably dimethylacetamide, acetonitrile or dimethyl sulphoxide; an ether, such as tetrahydrofuran or dioxane; a chlorinated solvent, such as dichloromethane, dichloroethane, chloroform or chlorobenzene; an ester, such as ethyl or methyl acetate; an apolar aprotic solvent, typically toluene; or a mixture of two or more, preferably two or three, of said solvents.

A base can be organic or inorganic, strong or weak, as described above. A base can be, for example, a cyclic or acyclic tertiary amine, such as triethylamine, or an alkali metal $C_1$-$C_6$ alkoxide, for example of sodium or potassium, preferably potassium tert-butoxide.

The reaction between a compound of formula (V) and a compound of formula (VI) is preferably carried out in the presence of toluene and triethylamine.

The reaction can be carried out at a temperature of between about 0° C. and the solvent reflux temperature, preferably between about 25° C. and about 100° C., and more preferably between about 35° C. and about 70° C.

A compound of formula (III) as defined above is novel, and is a further object of the invention.

Preferred compounds of formula (III) are those wherein $R_1$ is $(CH_3)_3$—Si— or Ts (tosyl) and Y is iodine.

A compound of formula (IV), as defined above, is known and can be prepared as described, for example, in U.S. Pat. No. 7,396,932 starting with para-methoxy aniline.

A compound of formula (V) can be prepared, for example, by decarboxylative hydrolysis of the compound of formula (VII) wherein Y is as defined above and Z is cyano or a COOR' group wherein R' is as defined above.

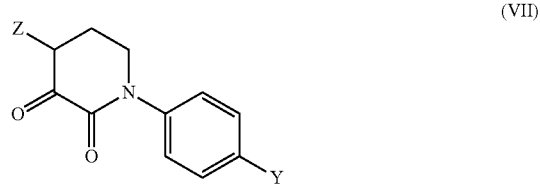

(VII)

The compound of formula (VII) can be prepared from inexpensive raw materials which are widely commercially available, by the methods described, for example, in U.S. Pat. No. 3,423,414.

Alternatively, a compound of formula (V) can be prepared, starting with the lactam of formula (VIII)

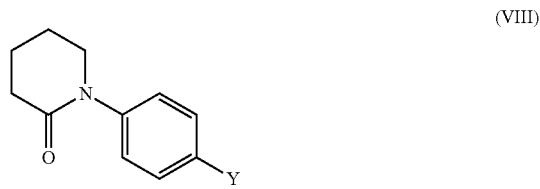

(VIII)

wherein Y is as defined above, as reported in U.S. Pat. No. 6,413,980. Said preparation can be performed, for example, by functionalisation in the alpha position of the lactam of formula (VIII), wherein Y is as defined above, and subsequent conversion to the ketolactam of formula (V).

The following examples illustrate the invention.

EXAMPLE 1

Synthesis of a compound of formula (III): 1-(4-Iodophenyl)-3-trimethylsilyloxy-5,6-dihydro-1H-pyridin-2-one (IIIa)

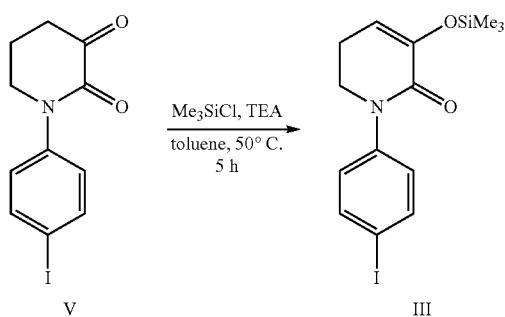

The compound of formula V (2.00 g, 6.35 mmol) is suspended in 15 ml of toluene in a 50 ml 3-necked flask equipped with coolant, thermometer and magnetic stirrer, in nitrogen atmosphere. Triethylamine (1.15 ml, 8.26 mmol) is added, and the mixture is cooled to 0° C. Chlorotrimethylsilane (0.97 ml, 7.64 mmol) is added drop by drop at a temperature of under 5° C. After the addition, the temperature is increased to 50° C., and after 5 h the reaction mixture is cooled to room temperature, diluted with toluene (30 ml) and washed with $H_2O$ (1×10 ml) and a saturated solution of NaCl (1×10 ml). The organic phase is anhydrified on ($Na_2SO_4$), filtered and evaporated under low pressure. Compound (III) is obtained as a brown solid (2.23 g, yield 90%), which is used for the next stage without further purification.

$^1$H NMR (300 MHz, CDCl$_3$): δ 7.67 (2H, dd, J=8.1 Hz, Ar—H), 7.06 (2H, dd, J=8.1 Hz, Ar—H), 5.81 (1H, t, J=4.8 Hz, CHCOSiMe$_3$), 3.77 (2H, t, J=6.9 Hz, N—CH$_2$), 2.48 (2H, m, CH$_2$CH$_2$CH), 0.23 (9H, s, CHCOSi(CH$_3$)$_3$).

EXAMPLE 2

Synthesis of a compound of formula (III): 1-(4-Iodophenyl)-3-toluenesulphonyl-5,6-dihydro-1H-pyridin-2-one

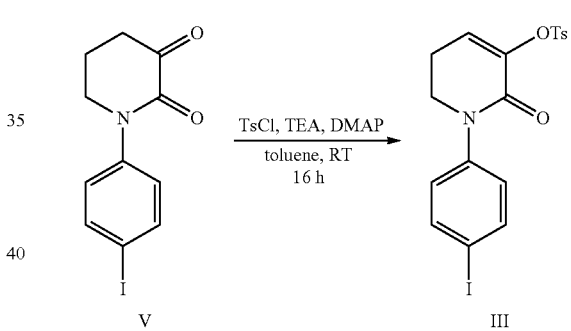

The compound of formula V (370 mg, 1.17 mmol) is suspended in 2.5 ml of toluene in a 25 ml 3-necked flask equipped with coolant, thermometer and magnetic stirrer, in nitrogen atmosphere. Triethylamine (0.250 ml, 1.80 mmol), dimethylaminopyridine (16 mg, 0.132 mmol) and tosyl chloride (240 mg 1.26 mmol) are then added in sequence. The reaction proceeds at room temperature; after 16 h the reaction mixture is diluted with 25 ml of AcOEt and washed with H70 (2×10 ml) and a saturated solution of NaCl (1×10 ml). The organic phase is anhydrified with Na$_2$SO$_4$, filtered and evaporated under low pressure. The compound of formula (III) is obtained as a brown solid (470 mg, yield 87%), which is used for the next stage without further purification.

$^1$H NMR (300 MHz, CDCl$_3$): δ7.92 (2H, dd, J$_O$=8.4 Hz, Ar—H), 7.66 (2H, dd, J$_O$=9.0 Hz, Ar—H), 7.31 (2H, dd, J$_O$=8.4 Hz, Ar—H), 6.96 (2H, dd, J$_O$=9.0 Hz, Ar—H), 6.66 (1H, t, J=4.5 Hz, CHCOTs), 3.82 (2H, t, J=6.9 Hz, N—CH$_2$), 2.65 (2H, dt, J$_1$=6.9 Hz, J$_2$=4.5 Hz CH$_2$CH$_2$CHOTs), 2.42 (3H, s, Ar—CH$_3$).

EXAMPLE 3

Synthesis of a compound of formula (IV): Chloro[(4-methoxyphenyl)hydrazono]acetic acid ethyl ester (IV)

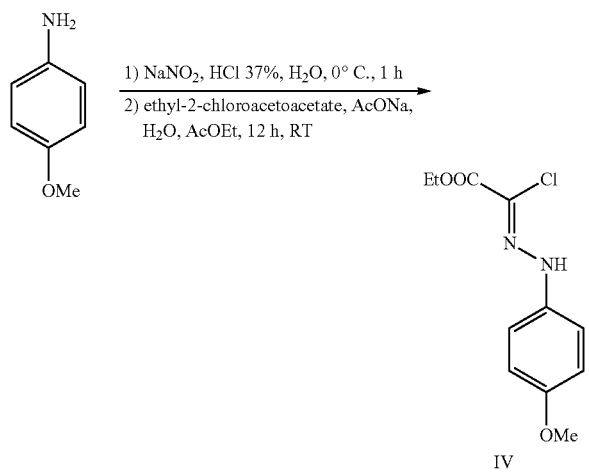

p-anisidine (31.02 g, 0.252 mol) in 100 ml of H₂O is suspended in a 250 ml 4-necked flask equipped with coolant, thermometer, dropping funnel and magnetic stirrer, and cooled to 0° C. in an ice bath. 60 ml of 37% HCl is added, followed by a solution of NaNO₂ (20.95 g, 0.307 mol) in 50 ml of H₂O, through a dropping funnel, maintaining the temperature below 5° C. After the addition the mixture is left under stirring at between 0 and 5° C. for 1 h, and the solution obtained is added at 0° C. to a solution containing ethyl-2-chloroacetoacetate (41.65 g, 0.254 mol), AcONa (47.84 g, 0.583 mol), AcOEt (200 ml) and H₂O (100 ml). The biphasic system is stirred at between 0 and 5° C. for 1 h, and then at about 25° C. for 16 h. The phases are then separated and the organic phase is washed with a saturated solution of NaHCO₃ (4×80 ml), anhydrified on Na₂SO₄, filtered and evaporated under low pressure. The compound of formula (IV) is obtained as a solid (about 57 g), which is used for the next stage without further purification.

$^1$H NMR (300 MHz, CDCl₃): δ8.24 (1H, s, N—H), 7.16 (2H, dd, J$_o$=9.0 Hz, Ar—H), 6.88 (2H, dd, J$_o$=9.0 Hz, Ar—H), 4.37 (2H, q, J=7.2 Hz, COOC$\underline{H}_2$CH₃), 3.79 (3H, s, Ar—OCH₃), 1.39 (3H, t, J=7.2 Hz, COOCH₂C$\underline{H}_3$).

EXAMPLE 4

Synthesis of a compound of formula (II): 1-(4-methoxyphenyl)-6-(4-iodophenyl)-7-oxo-4,5,6,7-tetrahydro-1H-pyrazolo[3,4-c]pyridine-3-carboxylic acid ethyl ester

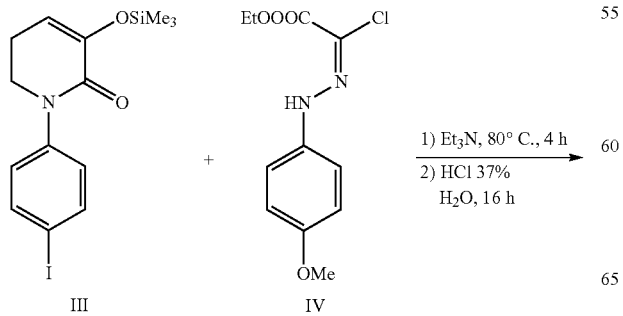

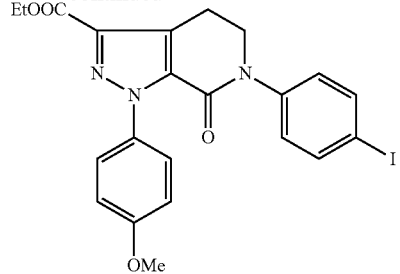

Compound (IV) (0.82 g, 3.19 mmol) is dissolved in 5 ml of AcOEt in a 25 ml 3-necked flask equipped with coolant, thermometer and magnetic stirrer, in nitrogen atmosphere, and cooled to 0° with an ice bath. Compound (III) (1.02 g, 2.63 mmol) and triethylamine (0.89 ml, 6.40 mmol) are added. When the additions have been completed, the reaction is heated to reflux temperature for 3 h, after which another portion of compound (IV) (350 mg) and triethylamine (0.25 ml) are added. When compound (III) has completely disappeared, the end-of-reaction mixture is cooled to 0° C., treated with a solution of HCl (1.80 g of 37% HCl in 3.20 g of H₂O) and maintained under stirring at room temperature overnight. A solid precipitates, which is filtered through a Buchner funnel and washed with 5 ml of a 1:1 solution of AcOEt and isopropanol. The compound of formula (II) is obtained as a solid (0.85 g, yield 63%).

$^1$H NMR (300 MHz, CDCl₃): δ7.67 (2H, dd, J$_o$=8.7 Hz, Ar—H), 7.46 (2H, dd, J$_o$=9.0 Hz, Ar—H), 7.06 (2H, dd, J$_o$=9.0 Hz, Ar—H), 6.90 (2H, dd, J$_o$=9.0 Hz, Ar—H), 4.45 (2H, q, J=7.2 Hz, COOC$\underline{H}_2$CH₃), 4.09 (2H, t, J=6.6 Hz, CH₂C$\underline{H}_2$N), 3.81 (3H, s, Ar—OCH₃), 3.32 (2H, t, J=6.6 Hz, C$\underline{H}_2$CH₂N), 1.43 (3H, t, J=7.3 Hz, COOCH₂C$\underline{H}_3$).

EXAMPLE 5

Synthesis of a compound of formula (II): 1-(4-methoxyphenyl)-6[4-(2-oxo-piperidinyl)phenyl]-7-oxo-4,5,6,7-tetrahydro-1H-pyrazolo[3,4-c]pyridine-3-carboxylic acid ethyl ester

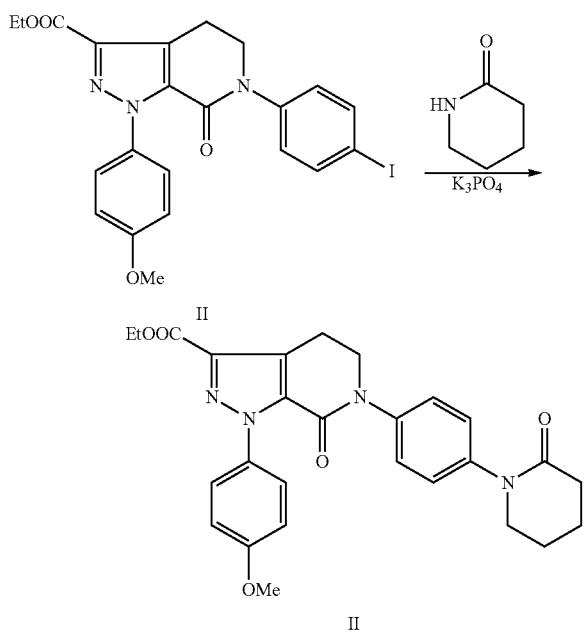

Compound II, prepared as in Example 4 (35.90 g, 69.40 mmol) is suspended in 250 ml of toluene in a 1 L 4-necked flask equipped with coolant, thermometer and magnetic stirrer, in nitrogen atmosphere. δ-valerolactam (13.74 g, 138.60 mmol), $K_3PO_4$ (30.25 g, 142.50 mmol) and CuI (2.54 g, 13.34 mmol) are then added in sequence. The suspension obtained is degassed 3 times at room temperature; N,N'-dimethylethylenediamine (1.65 ml, 26.78 mmol) is then added and the mixture is heated to reflux temperature. After 48 h the end-of-reaction mixture is filtered through a Buchner funnel, and the filter is washed with 200 ml of toluene. The toluene phase is washed with a solution of $Na_2S_2O_3$ (50 g in 160 ml of $H_2O$, 2×80 ml), 15% $NH_3$ (2×80 ml) and a saturated solution of NaCl (1×80 ml). The organic phase is anhydrified on ($Na_2SO_4$), filtered and evaporated under low pressure. A solid product is obtained (37 g), which is crystallised by AcOEt. After crystallisation the product is obtained as a pure white solid (22.7 g, yield 67%).

$^1$H NMR (300 MHz, DMSO-d6): δ7.47 (2H, dd, $J_o$=8.7 Hz, Ar—H), 7.32 (2H, dd, $J_o$=9.0 Hz, Ar—H), 7.28 (2H, dd, $J_o$=8.7 Hz, Ar—H), 6.90 (2H, dd, $J_o$=9.0 Hz, Ar—H), 4.32 (2H, q, J=6.9 Hz, COOC$\underline{H}_2$CH$_3$), 4.06 (2H, t, J=6.6 Hz, CH$_2$C$\underline{H}_2$N), 3.79 (3H, s, Ar—OCH$_3$), 3.57 (2H, m, NC$\underline{H}_2$CH$_2$CH$_2$CO) 3.19 (2H, t, J=6.6 Hz, C$\underline{H}_2$CH$_2$N), 2.36 (2H, m, NCH$_2$CH$_2$C$\underline{H}_2$CO), 1.83 (4H, m, NCH$_2$C$\underline{H}_2$C$\underline{H}_2$CO), 1.31 (3H, t, J=6.9 Hz, COOCH$_2$C$\underline{H}_3$).

EXAMPLE 6

Synthesis of compound of formula (I): 1-(4-Methoxyphenyl)-6-[4-(2-oxo-piperidinyl)phenyl]-7-oxo-4,5,6,7-tetrahydro-1H-pyrazolo[3,4-c]pyridine-3-carboxyamide: Apixaban (I)

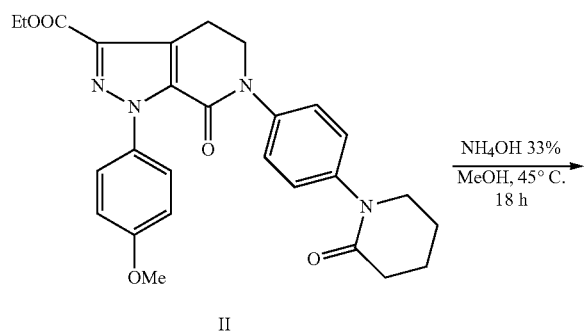

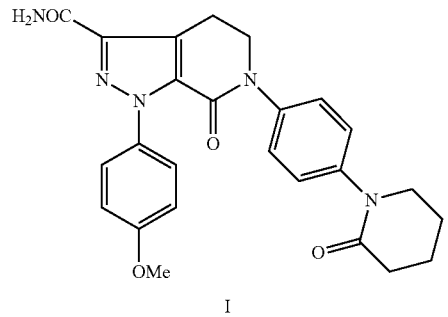

The compound of formula II, prepared as in Example 5 (17.50 g, 35.82 mmol), is suspended in 100 ml of 33% $NH_3$ and 200 ml of MeOH in a 1 L 4-necked flask equipped with coolant, thermometer and magnetic stirrer, in nitrogen atmosphere, and heated to 45°. MeOH (250 ml) is added until completely dissolved, and the solution is left under stirring for 2 h. Another addition of 33% $NH_3$ (50 ml) is performed, and the progress of the reaction is monitored by TLC (AcOEt/MeOH 9:1) and HPLC. After 18 h the solvent is evaporated under low pressure, and the solid residue obtained is suspended in 200 ml of $H_2O$ and left under stirring for 2 h. The white solid is filtered through a Büchner funnel, and washed with $H_2O$ (50 ml). The product of formula (I) is stove-dried at 50° C. to a constant weight (12.60 g, yield 76%). The HPLC purity of the product exceeds 99%.

$^1$H NMR (300 MHz, CDCl$_3$): δ7.47 (2H, dd, $J_o$=8.7 Hz, Ar—H), 7.31 (2H, dd, $J_o$=8.7 Hz, Ar—H), 7.23 (2H, dd, $J_o$=8.7 Hz, Ar—H), 6.93 (2H, dd, $J_o$=8.7 Hz, Ar—H), 6.83 (1H, s, N—H), 5.53 (1H, s, N—H), 4.11 (2H, t, J=6.6 Hz, CH$_2$C$\underline{H}_2$N), 3.81 (3H, s, Ar—OCH$_3$), 3.59 (2H, m, NC$\underline{H}_2$CH$_2$CH$_2$CO) 3.37 (2H, t, J=6.6 Hz, C$\underline{H}_2$CH$_2$N), 2.55 (2H, m, NCH$_2$CH$_2$CH$_2$C$\underline{H}_2$CO), 1.93 (4H, m, NCH$_2$C$\underline{H}_2$C$\underline{H}_2$CO).

EXAMPLE 7

Preparation of Apixaban of Formula (I), Crystalline Form α

1.6 g of apixaban crystalline form H2-2 is suspended in 25 ml acetone, and the dispersion is heated to the reflux temperature of the solvent. A further about 25 ml of acetone is added slowly to facilitate stirring. The dispersion is then cooled to room temperature. The solid is recovered by filtration through a Bückner funnel. The solid is then air-dried to eliminate the excess solvent.

The crystalline solid presents an XRPD with the following main peaks in 2θ [°] (with CuKα radiation): 6.0, 7.1, 11.0, 11.9, 12.9, 13.6, 15.1, 16.1, 17.6, 19.1, 20.3, 21.6, 22.7, 24.5, 26.0, 26.7, 27.2, 28.8 and 30.1°, as shown in FIG. 1; a DSC trace as shown in FIG. 2; a water content of between about 5 and 6% w/w; crystals having a $D_{50}$ value of between about 25 and 250 μm; and a purity equal to or greater than 99.9%.

EXAMPLE 8

Preparation of Apixaban of Formula (I), Crystalline Form α

0.5 g of apixaban crystalline form H2-2 is suspended in 25 ml acetone, and the dispersion is heated to the reflux temperature of the solvent. The dispersion is then cooled to room temperature. The solid is recovered by filtration through a Bückner funnel.

XRPD: Main peaks in 2θ [°] (with CuKα radiation): 6.0, 7.1, 11.0, 11.9, 12.9, 13.6, 15.1, 16.1, 17.6, 19.1, 20.3, 21.6, 22.7, 24.5, 26.0, 26.7, 27.2, 28.8 and 30.1°.

The invention claimed is:

1. A process for the preparation of a compound of formula (II), as a single stereoisomer or a mixture thereof, or a salt thereof

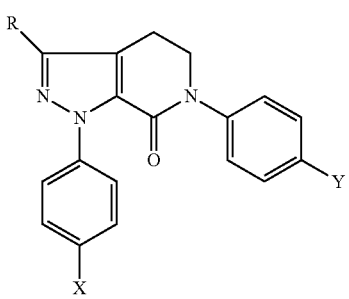

(II)

wherein each of X and Y, being the same or different, is an optionally substituted $C_1$-$C_{12}$ alkyl group; an optionally substituted $C_3$-$C_{12}$ cycloalkyl group; an optionally substituted aryl group; an optionally substituted $C_1$-$C_{12}$ alkoxy group; a halogen; hydroxy; cyano; nitro; an amine group —NR'R" or an amide group —NR'COR", wherein each of R' and R", which are the same or different, is hydrogen, an optionally substituted $C_1$-$C_{12}$ alkyl group, an optionally substituted $C_3$-$C_{12}$ cycloalkyl group, an optionally substituted aryl group, or R' and R", taken together, complete a heterocyclic $C_2$-$C_7$ ring;

R is an optionally substituted $C_1$-$C_{12}$ alkyl group; an optionally substituted $C_3$-$C_{12}$ cycloalkyl group; an optionally substituted aryl group; cyano; a COOR' group, wherein R' is as defined above; a —CONR'R" group, wherein each of R' and R", which are the same or different, is as defined above;

comprising a cycloaddition reaction between a compound of formula (III)

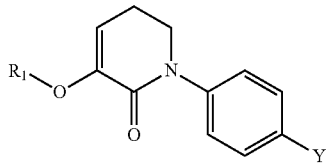

(III)

wherein $R_1$ is an optionally substituted $C_3$-$C_{12}$ cycloalkyl group; an optionally substituted aryl-$C_1$-$C_{12}$ alkyl group; a silyl group of formula $(R_2)_3Si$—, wherein each $R_2$, which are the same or different, is selected from the group consisting of an optionally substituted $C_1$-$C_{12}$ alkyl, optionally substituted $C_3$-$C_{12}$ cycloalkyl, optionally substituted $C_1$-$C_{12}$ alkoxy and optionally substituted aryl; or a sulphonyl group $R_3SO_2$—, wherein $R_3$ is an optionally substituted $C_1$-$C_{12}$ alkyl group, an optionally substituted $C_3$-$C_{12}$ cycloalkyl group, an optionally substituted aryl group, an optionally substituted aryl-$C_1$-$C_{12}$ alkyl group; or an $R_3CO$— acyl group wherein $R_3$ is as defined above, and Y is defined above;

and a compound of formula (IV),

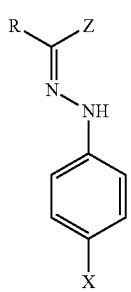

(IV)

wherein R is an optionally substituted $C_3$-$C_{12}$ cycloalkyl group; an optionally substituted aryl-$C_1$-$C_{12}$ alkyl group; a silyl group of formula $(R_2)_3Si$—, wherein each $R_2$, which are the same or different, is selected from the group consisting of an optionally substituted $C_1$-$C_{12}$ alkyl, optionally substituted $C_3$-$C_{12}$ cycloalkyl, optionally substituted $C_1$-$C_{12}$ alkoxy and optionally substituted aryl; or a sulphonyl group $R_3SO_2$—, wherein $R_3$ is an optionally substituted $C_1$-$C_{12}$ alkyl group, an optionally substituted $C_3$-$C_{12}$ cycloalkyl group, an optionally substituted aryl group; an optionally substituted aryl-$C_1$-$C_{12}$ alkyl group; or an $R_3CO$— acyl group wherein $R_3$ is as defined above;

Z is halogen or a sulphonyl group of formula $R_3SO_2$—O—, wherein $R_3$ is as defined above; and R, X and Y are as defined above; and, optionally converting a compound of formula (II) to another compound of formula (II), and/or resolving a mixture of stereoisomers into a single stereoisomer of formula (II), and/or converting a compound of formula (II) to a salt thereof, and/or converting a salt of a compound of formula (II) to an unsalified compound of formula (II).

2. The process of claim 1, wherein the cycloaddition reaction is carried out in the presence of a solvent selected from the group consisting of a polar aprotic solvent; an ether; a chlorinated solvent; an ester; an apolar aprotic solvent; a polar protic solvent; water or a mixture of two or more of said solvents.

3. The process of claim 1, wherein the cycloaddition reaction is carried out in the presence of an organic or inorganic base selected from the group consisting of a cyclic or acyclic tertiary amine, an alkali metal $C_1$-$C_6$ alkoxide, an alkali metal carbonate, an alkali metal hydroxide and an alkali metal hydride.

4. The process of claim 1, wherein the cycloaddition reaction is carried out in the presence of ethyl acetate and triethylamine.

5. The process of claim 1, wherein the cycloaddition reaction is carried out at a temperature of between about 0° C. and the reflux temperature of the solvent used.

6. The process of claim 1, wherein the cycloaddition reaction is carried out at a temperature between about 40° C. and about 85° C.

7. The process of claim 1, further comprising treating the reaction mixture with an aqueous acid subsequent to the cycloaddition reaction if $R_1$ is an optionally substituted $C_3$-$C_{12}$ cycloalkyl group, optionally substituted aryl-$C_1$-$C_{12}$ alkyl, or a silyl group of formula $(R_2)_3Si$— in a compound of formula (III).

8. The process of claim 1, further comprising the preparation of a compound of formula (III) by a process comprising the reaction between a ketolactam of formula (V),

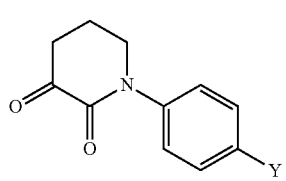

(V)

wherein Y is as defined as in claim 1,
and a compound of formula (VI)

$R_1W$ (VI)

wherein $R_1$ is as defined in claim 1 and W is a leaving group.

9. The process of claim 7, wherein a compound of formula (VI) is (CH$_3$)$_3$—SiCl or TsCl (tosyl chloride).

10. The process of claim 1, wherein a compound of formula (II) is apixaban of formula (I)

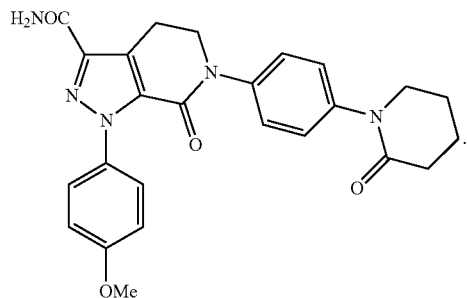

(I)

11. The process of claim 10, wherein apixaban of formula (I) is crystalline form α characterized by an XRPD spectrum wherein the most intense peaks are found at 6.0, 7.1, 11.0, 11.9, 12.9, 13.6, 15.1, 16.1, 17.6, 19.1, 20.3, 21.6, 22.7, 24.5, 26.0, 26.7, 27.2, 28.8 and 30.1° in 2θ and having a DSC trace wherein the main thermal events are found at about 60-110° C. (endothermy), 145-155° C. (endothermy), 175-185° C. (exothermy), and 234° C. (melting endothermy).

12. The process of claim 11, wherein apixaban of formula (I) in crystalline form α has a water content of between about 3 and 7% w/w.

13. The process of claim 12, wherein the crystalline form α of apixaban has a water content of between about 4.5 and 6.5% w/w.

* * * * *